US008795573B2

(12) United States Patent
Bracken et al.

(10) Patent No.: US 8,795,573 B2
(45) Date of Patent: Aug. 5, 2014

(54) POLYURETHANE/POLYISOPRENE BLEND CATHETER

(75) Inventors: Ronald L. Bracken, Oxford, GA (US); Fung Bor Chen, Greer, SC (US); Randy Tuck, Summerville, SC (US)

(73) Assignee: C.R. Bard, Inc., Covington, GA (US)

( * ) Notice: Subject to any disclaimer, the term of this patent is extended or adjusted under 35 U.S.C. 154(b) by 548 days.

(21) Appl. No.: 13/000,821

(22) PCT Filed: Jun. 30, 2009

(86) PCT No.: PCT/US2009/049293
§ 371 (c)(1),
(2), (4) Date: Apr. 6, 2011

(87) PCT Pub. No.: WO2010/002914
PCT Pub. Date: Jan. 7, 2010

(65) Prior Publication Data
US 2011/0178507 A1    Jul. 21, 2011

Related U.S. Application Data

(60) Provisional application No. 61/076,933, filed on Jun. 30, 2008.

(51) Int. Cl.
C08L 75/04        (2006.01)
(52) U.S. Cl.
USPC .......................... 264/306; 264/304; 264/301
(58) Field of Classification Search
USPC .......................................... 264/301, 304, 306
See application file for complete search history.

(56) References Cited

U.S. PATENT DOCUMENTS

| 3,067,180 A | 12/1962 | Miller et al. |
| 3,223,134 A | 12/1965 | Hofmann |
| 3,718,628 A | 2/1973 | Boyer |
| 3,965,077 A | 6/1976 | Son |

(Continued)

FOREIGN PATENT DOCUMENTS

| EP | 0 093 093 B2 | 11/1991 |
| EP | 0 009 15133 A1 | 5/1999 |

(Continued)

OTHER PUBLICATIONS

Extended European Search Report dated Apr. 15, 2013 for PCT/US2009049293.

(Continued)

Primary Examiner — Galen Hauth
(74) Attorney, Agent, or Firm — Knobbe Martens Olson & Bear, LLP

(57) ABSTRACT

A medical article, such as a catheter, is formed from a blend of polyurethane and synthetic polyisoprene (SPIR). The blended medical article is preferably selected and prepared to be relatively rigid at room temperature and relatively flexible at body temperature. An intermittent catheter made from the blend provides a degree of stiffness for its insertion into the patient at room temperature. The catheter becomes softer, and therefore more comfortable, at warmer temperatures (e.g., body temperature) which reduce discomfort after insertion. Optionally, the catheter or a portion thereof can have a hydrophilic coating as to avoid the need for external lubricants. Advantageously, the blended catheter can meet the stiffness, tensile strength, and coefficient of friction requirements of intermittent catheterization applications while avoiding the risk of toxic or allergic reactions in sensitive users.

16 Claims, 4 Drawing Sheets

(56) References Cited

U.S. PATENT DOCUMENTS

| | | | |
|---|---|---|---|
| 4,110,240 A | 8/1978 | Leo et al. |
| 4,128,539 A | 12/1978 | Onizawa |
| 4,146,689 A | 3/1979 | Onizawa |
| 4,172,939 A | 10/1979 | Hoh |
| 4,222,384 A | 9/1980 | Birtwell |
| 4,237,247 A | 12/1980 | Matoba |
| 4,248,985 A | 2/1981 | Ohishi |
| 4,271,049 A | 6/1981 | Coran |
| 4,338,410 A | 7/1982 | Ueno et al. |
| 4,588,752 A | 5/1986 | Kmiec |
| 4,687,756 A | 8/1987 | Okamoto et al. |
| 4,725,650 A | 2/1988 | Landi |
| 4,855,364 A | 8/1989 | Sandstrom |
| 4,861,842 A | 8/1989 | Cohen et al. |
| 4,870,135 A | 9/1989 | Mowdood et al. |
| 4,906,237 A | 3/1990 | Johansson |
| 4,948,840 A | 8/1990 | Berta |
| 4,983,685 A | 1/1991 | Aoshima et al. |
| 5,036,133 A | 7/1991 | Coran |
| 5,096,978 A | 3/1992 | Coran |
| 5,158,997 A | 10/1992 | Berta |
| 5,160,790 A | 11/1992 | Elton |
| 5,256,738 A | 10/1993 | Chasser et al. |
| 5,290,585 A | 3/1994 | Elton |
| 5,342,900 A | 8/1994 | Wolpers |
| 5,356,997 A | 10/1994 | Massie, II et al. |
| 5,374,689 A | 12/1994 | Rostek, Jr. |
| 5,382,629 A | 1/1995 | Coran |
| 5,473,017 A | 12/1995 | Wang |
| 5,545,451 A | 8/1996 | Huang |
| 5,554,699 A | 9/1996 | Layer et al. |
| 5,601,870 A | 2/1997 | Haung |
| 5,609,583 A | 3/1997 | Hakki et al. |
| 5,612,083 A | 3/1997 | Haung |
| 5,662,960 A | 9/1997 | Hostettler |
| 5,674,277 A | 10/1997 | Freitag |
| 5,770,632 A | 6/1998 | Sekhar et al. |
| 5,783,633 A | 7/1998 | Sperling |
| 5,786,426 A * | 7/1998 | Sperling et al. ............... 525/131 |
| 5,800,412 A | 9/1998 | Zhang |
| 5,869,591 A | 2/1999 | McKay |
| 5,872,173 A | 2/1999 | Anand |
| 5,876,624 A | 3/1999 | Novits et al. |
| 5,916,956 A | 6/1999 | Wang et al. |
| 5,919,570 A | 7/1999 | Hostettler |
| 6,057,044 A | 5/2000 | Rennar |
| 6,071,996 A | 6/2000 | Davis |
| 6,075,092 A | 6/2000 | Nakamura |
| 6,096,013 A | 8/2000 | Hakky et al. |
| 6,120,904 A | 9/2000 | Hostettler |
| 6,187,829 B1 | 2/2001 | Sellers |
| 6,187,857 B1 | 2/2001 | Ozawa et al. |
| 6,191,192 B1 | 2/2001 | Monden |
| 6,193,699 B1 | 2/2001 | Matsumoto |
| 6,221,447 B1 | 4/2001 | Munn |
| 6,238,799 B1 | 5/2001 | Opolski |
| 6,241,409 B1 | 6/2001 | Holloway |
| 6,329,444 B1 | 12/2001 | McGlothlin |
| 6,365,657 B1 | 4/2002 | Goto et al. |
| 6,372,856 B2 | 4/2002 | Ozawa et al. |
| 6,391,409 B1 | 5/2002 | Yeh |
| 6,420,488 B1 | 7/2002 | Penot |
| 6,422,997 B1 | 7/2002 | Green et al. |
| 6,451,893 B1 | 9/2002 | Tao |
| 6,476,154 B1 | 11/2002 | Maly |
| 6,521,691 B1 | 2/2003 | Agostini et al. |
| 6,523,585 B1 | 2/2003 | Ducci |
| 6,536,492 B2 | 3/2003 | Vasseur |
| 6,541,574 B1 | 4/2003 | Takemura |
| 6,613,831 B1 | 9/2003 | Bentley et al. |
| 6,618,861 B2 | 9/2003 | Saks et al. |
| 6,629,961 B1 | 10/2003 | Israelsson |
| 6,648,854 B1 | 11/2003 | Patterson et al. |
| 6,648,863 B2 | 11/2003 | Reever |
| 6,653,380 B2 | 11/2003 | Dzikowicz |
| 6,673,404 B1 | 1/2004 | Yeh et al. |
| 6,732,734 B2 | 5/2004 | Ogushi et al. |
| 6,747,099 B1 | 6/2004 | Novits et al. |
| 6,753,374 B1 | 6/2004 | Hannon et al. |
| 6,756,449 B2 | 6/2004 | Benz |
| 6,828,387 B2 | 12/2004 | Wang et al. |
| 6,858,680 B2 | 2/2005 | Gunatillake |
| 6,872,763 B2 | 3/2005 | Andriolo |
| 6,894,082 B2 | 5/2005 | Brantl |
| 6,916,309 B2 | 7/2005 | Fangrow, Jr. |
| 6,920,643 B2 | 7/2005 | McGlothlin |
| 6,951,897 B2 | 10/2005 | Penot |
| 6,972,307 B2 | 12/2005 | Zimmer et al. |
| 6,982,050 B2 | 1/2006 | Chauvin et al. |
| 6,984,689 B2 | 1/2006 | Penot et al. |
| 7,008,979 B2 | 3/2006 | Schottman |
| 7,025,753 B2 | 4/2006 | Reever |
| 7,040,404 B2 | 5/2006 | Brothers |
| 7,041,746 B2 | 5/2006 | Dzikowicz |
| 7,048,977 B2 | 5/2006 | Dzikowicz |
| 7,148,279 B2 | 12/2006 | Voorheis |
| 7,176,260 B2 | 2/2007 | Tao |
| 7,196,129 B2 | 3/2007 | Migliarini et al. |
| 7,279,532 B2 | 10/2007 | Sasagawa |
| 7,282,041 B2 | 10/2007 | Igarashi |
| 7,294,678 B2 | 11/2007 | McGlothlin |
| 7,368,490 B2 | 5/2008 | Patel |
| 7,374,711 B2 | 5/2008 | McGlothlin |
| 7,441,574 B2 | 10/2008 | Koster |
| 7,528,181 B2 | 5/2009 | Bailey et al. |
| 7,572,850 B2 | 8/2009 | Hetzel |
| 7,700,705 B2 | 4/2010 | Jole |
| 2001/0004653 A1 | 6/2001 | Ozawa et al. |
| 2001/0037097 A1 | 11/2001 | Cheng et al. |
| 2002/0042465 A1 | 4/2002 | Migliarini |
| 2002/0045868 A1 | 4/2002 | Reever |
| 2002/0115767 A1 | 8/2002 | Cruse |
| 2002/0160134 A1 | 10/2002 | Ogushi et al. |
| 2002/0173563 A1 | 11/2002 | Wang et al. |
| 2002/0193501 A1 | 12/2002 | Rajaraman |
| 2003/0055169 A1 | 3/2003 | Amino |
| 2003/0073977 A1 | 4/2003 | Charles |
| 2003/0088002 A1 | 5/2003 | Dzikowicz |
| 2003/0116319 A1 | 6/2003 | Brothers |
| 2003/0121659 A1 | 7/2003 | Brothers |
| 2003/0139524 A1 * | 7/2003 | Hochgesang ............... 524/571 |
| 2003/0139730 A1 | 7/2003 | Bracken et al. |
| 2003/0141633 A1 | 7/2003 | McGlothlin |
| 2003/0161975 A1 | 8/2003 | Lucas |
| 2003/0175458 A1 | 9/2003 | Jain |
| 2003/0204008 A1 | 10/2003 | Campion |
| 2004/0045095 A1 | 3/2004 | Manzoni |
| 2004/0054038 A1 | 3/2004 | Andriolo |
| 2004/0059305 A1 | 3/2004 | Reever |
| 2004/0063832 A1 | 4/2004 | Dzikowicz |
| 2004/0071909 A1 | 4/2004 | McGlothlin |
| 2004/0087712 A1 | 5/2004 | Rajaraman |
| 2004/0106743 A1 | 6/2004 | Chauvin et al. |
| 2004/0133156 A1 | 7/2004 | Diaz |
| 2004/0152811 A1 | 8/2004 | Lin et al. |
| 2004/0158208 A1 | 8/2004 | Hiejima |
| 2004/0169317 A1 * | 9/2004 | Wang et al. .................. 264/301 |
| 2004/0235587 A1 | 11/2004 | Sullivan |
| 2004/0241085 A1 | 12/2004 | Marx |
| 2004/0259974 A1 | 12/2004 | Scott |
| 2005/0027054 A1 | 2/2005 | Zimmer |
| 2005/0048121 A1 * | 3/2005 | East et al. .................... 424/486 |
| 2005/0065249 A1 | 3/2005 | Dzikowicz |
| 2005/0080150 A1 | 4/2005 | Nakahama et al. |
| 2005/0147655 A1 | 7/2005 | Bagwell |
| 2005/0155687 A1 | 7/2005 | Amaddeo |
| 2006/0014862 A1 | 1/2006 | Dzikowicz |
| 2006/0047269 A1 | 3/2006 | Reever et al. |
| 2006/0059604 A1 | 3/2006 | Lei |
| 2006/0068138 A1 | 3/2006 | Janssen |
| 2006/0099237 A1 | 5/2006 | Modak et al. |
| 2006/0135951 A1 | 6/2006 | Meek et al. |
| 2006/0160922 A1 | 7/2006 | Scott |
| 2006/0173137 A1 | 8/2006 | McGlothlin |

(56) References Cited

U.S. PATENT DOCUMENTS

| | | |
|---|---|---|
| 2006/0251694 A1 | 11/2006 | Nielsen |
| 2007/0032780 A1 | 2/2007 | Wang |
| 2007/0054993 A1 | 3/2007 | Kanz et al. |
| 2007/0054994 A1 | 3/2007 | Kanz |
| 2007/0112313 A1 | 5/2007 | Fangrow |
| 2007/0207186 A1 | 9/2007 | Scanlon |
| 2007/0231522 A1 | 10/2007 | Sakazaki |
| 2007/0287800 A1 | 12/2007 | Acquarulo |
| 2008/0045678 A1 | 2/2008 | Koster |
| 2008/0161452 A1 | 7/2008 | York |
| 2008/0161475 A1 | 7/2008 | York |
| 2008/0173379 A1 | 7/2008 | Mergell |
| 2008/0190322 A1 | 8/2008 | Chen |
| 2008/0221246 A1 | 9/2008 | Imam |
| 2008/0306200 A1 | 12/2008 | Chen |
| 2008/0311409 A1 | 12/2008 | Lipinski |
| 2009/0054551 A1 | 2/2009 | Meissner |
| 2009/0111923 A1 | 4/2009 | Jiang |
| 2009/0176601 A1 | 7/2009 | Snell |
| 2009/0234064 A1 | 9/2009 | Wang et al. |
| 2009/0272384 A1 | 11/2009 | Lucas et al. |
| 2009/0326102 A1 | 12/2009 | Wang |
| 2011/0028943 A1 | 2/2011 | Lawson et al. |

FOREIGN PATENT DOCUMENTS

| | | |
|---|---|---|
| EP | 1 714 665 | 10/2006 |
| JP | 1-166310 | 11/1989 |
| JP | 03-031335 | 2/1991 |
| JP | 408020675 | 1/1996 |
| JP | 2001-19802 | 1/2001 |
| JP | 2002-282365 | 10/2002 |
| JP | 2004-113474 | 4/2004 |
| JP | 2004-290366 | 10/2004 |
| JP | 2006-056862 | 2/2006 |
| WO | WO 89/03860 A1 | 5/1989 |
| WO | WO 01/72158 | 10/2001 |
| WO | WO 02/090430 | 11/2002 |
| WO | WO2005/003237 | 1/2005 |
| WO | WO 2005/035589 | 4/2005 |
| WO | WO 2007/017368 | 2/2007 |
| WO | WO 2007/017375 | 2/2007 |

OTHER PUBLICATIONS

JP 03-031335 A (1991), USPTO partial translation prepared by Phoenix Translations.

Senyek, M.L., "Isoprene Polymers," in: Encyclopedia of Polymer Science and Technology, 2008, pp. 56-57.

International Search Report and Written Opinion for International application No. PCT/US2009/049293, mailed Aug. 31, 2009.

Dzikowicz, "Latexes," (Vanderbilt Published Articles, Papers and Presentations, Norwalk, CT, R. T. Vanderbilt Co, Inc.), 2003.

* cited by examiner

FIG. 1
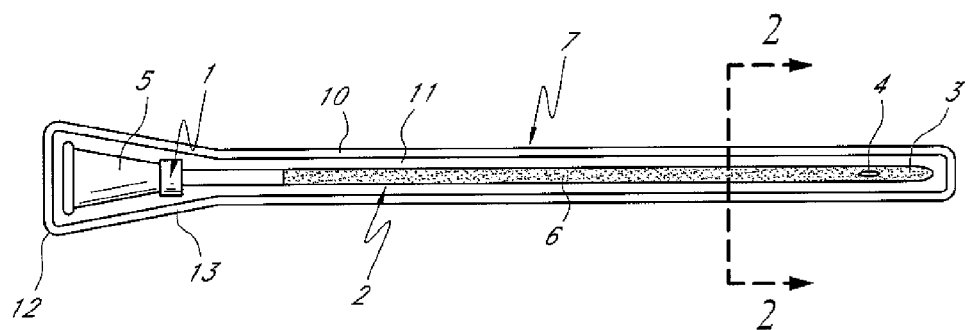
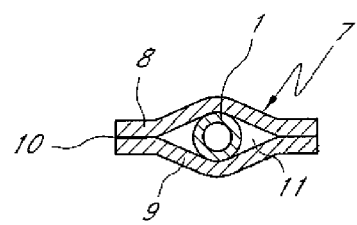
FIG. 2

POLYURETHANE/POLYISOPRENE BLEND CATHETER

RELATED APPLICATION

This application is the National Stage of International Application No. PCT/US2009/049293, filed on Jun. 30, 2009, entitled "POLYURETHANE/POLYISOPRENE BLEND CATHETER," which claims the benefit of U.S. Provisional Application No. 61/076,933, filed Jun. 30, 2008, entitled "POLYURETHANE/POLYISOPRENE BLEND CATHETER," the disclosure of each of which is hereby incorporated by reference in its entirety.

BACKGROUND OF THE INVENTION

1. Field of the Invention

This application relates to catheters, for example urinary catheters, such as indwelling and intermittent catheters, and relates more specifically to intermittent catheters comprising a hypoallergenic or non-allergenic, synthetic polyisoprene based formulation.

2. Description of the Related Art

Catheters suitable for draining the bladder include both intermittent and indwelling catheters. Indwelling catheters include Foley catheters. Foley catheterization is typically indicated for surgical and medical patients who require, at least temporarily, assisted bladder voiding. Common indications to catheterize a patient include acute or chronic urinary retention (which can damage the kidneys), medical procedures (i.e., surgeries) that may at least temporarily limit a patient's movement, the need for accurate monitoring of input and output (such as in an ICU), benign prostatic hyperplasia, incontinence, and the effects of various surgical interventions involving the bladder and prostate.

A standard Foley catheter design includes a balloon disposed at the distal end of the catheter to anchor the catheter in the bladder. The catheter includes at least one lumen to drain urine from the bladder and at least one lumen to inflate the balloon (e.g., with sterile water). The proximal end of the Foley catheter includes at least two ports in communication with the two lumens. A first port is connected to the drainage lumen and has an interface with fittings for drainage and sampling. A second port is connected to the inflation lumen with a valve to ensure the inflation fluid remains within the lumen and balloon once filled. The tip of a standard Foley catheter extends beyond the sides of the balloon into the bladder and includes one or more apertures or "eyes" to drain fluids and debris from the bladder. This standard design has not changed in many years, although catheters with various additions (e.g., mechanical anchors, etc.) and improvements have been proposed and investigated.

A typical intermittent catheter differs from an indwelling catheter primarily in that the intermittent catheter does not have a retention balloon or an associated inflation lumen. Rather, the intermittent catheter is typically a single-lumen device, with multiple drainage eyes at the proximal end and a funnel at the distal end. Intermittent catheterization is often performed in individuals with malfunctioning urinary systems (e.g., suffering from strictures and traumas), as well as disabled individuals (e.g., para- or quadriplegics) who may be unable to voluntarily urinate. Such individuals will often self-catheterize with an intermittent catheter several times daily.

Intermittent catheters are generally catheters or tubes having a rounded tip connected to a distal end that is inserted into the bladder of a user or user. A molded funnel connected to a proximal end remains outside the body of the user. These types of catheters are typically utilized on a temporary, as-needed basis to remove urine from the bladder of a user. The distal tip may include slots or openings in the shaft to facilitate drainage of urine therefrom once the tip is positioned inside the bladder.

Intermittent catheters are typically disposable, although intermittent catheters exist which are designed to be cleaned and reused. Intermittent catheters are typically manufactured from natural rubber latex, or, in some cases, polyvinyl chloride (PVC). Pre-wetted intermittent catheters are intermittent catheters having a lubricious coating on an outer surface thereof. Pre-wetted catheters are either packaged in a wetting fluid or packaged dry and soaked in a wetting fluid after they are removed from their packaging in order to provide a catheter with a slippery outer surface to facilitate insertion into the user.

SUMMARY OF THE INVENTION

An aspect of the invention is directed to an intermittent urinary drainage catheter that includes a polyurethane and synthetic polyisoprene blend that is more resistant to deformation at a first temperature than when at a second temperature so as to provide a degree of stiffness for insertion of the catheter when the catheter is at the first temperature while reducing discomfort after insertion when the catheter is at the second temperature. The catheter having a 300% Young's Modulus between about 18° C. and about 25° C. ranging from about 200 psi to about 2000 psi. In another embodiment, at least a portion of the catheter has a hydrophilic outer surface.

Another aspect of the invention is directed to a blended medical article that includes a polyurethane material and a synthetic polyisoprene. The rigidity of the blended medical article varies with temperature.

Another aspect of the invention is directed to an intermittent urinary drainage catheter that is more flexible at a higher temperature than at a lower temperature. In an embodiment of such an aspect, the lower temperature is room temperature and the higher temperature is body temperature.

Another aspect of the invention is directed to a method of manufacturing a medical article that includes mixing synthetic polyisoprene with compounding ingredients to produce compounded synthetic polyisoprene, allowing the compounded synthetic polyisoprene to mature, and mixing the compounded synthetic polyisoprene with polyurethane to form a blend. The method further includes dipping a mold in the blend to form a medical article. The rigidity of the blended medical article varies with temperature.

Another aspect is directed to a composition comprising a synthetic polyisoprene latex, an accelerator system comprising a carbamate and a thiazole, a vulcanizing system comprising sulfur and a sulfur donor, and a polyurethane.

Another aspect is directed to a method for forming an elastomeric article that includes forming a film from a composition comprising a synthetic polyisoprene latex, an accelerator system having a carbamate and a thiazole as the accelerators, a vulcanizing system comprising sulfur and a sulfur donor, and polyurethane.

Another aspect is directed to a composition comprising a synthetic polyisoprene latex, an accelerator system comprising a carbamate and a thiazole and a vulcanizing system comprising sulfur, and polyurethane.

Another aspect is directed to a method for forming an elastomeric article that includes forming a film from a composition comprising a synthetic polyisoprene latex, an accelerator system having a carbamate and a thiazole as the accelerators, a vulcanizing system comprising sulfur, and polyurethane.

Another aspect is directed to a composition comprising a synthetic polyisoprene latex, an accelerator system comprising a carbamate and a vulcanizing system comprising sulfur and sulfur donor, and polyurethane.

Another aspect is directed to a method for forming an elastomeric article that includes forming a film from a composition comprising a synthetic polyisoprene latex, an accelerator system having a carbamate as the accelerator, a vulcanizing system comprising sulfur and sulfur donor, and polyurethane.

Another aspect is directed to a composition comprising a synthetic polyisoprene latex, an accelerator system comprising a carbamate and a vulcanizing system comprising sulfur, and polyurethane.

Another aspect is directed to a method for forming an elastomeric article that includes forming a film from a composition comprising a synthetic polyisoprene latex, an accelerator system having a carbamate as the accelerator, a vulcanizing system comprising sulfur, and polyurethane.

Another aspect is directed to a composition comprising a synthetic polyisoprene latex, an accelerator system comprising a carbamate and a guanidine and a vulcanizing system comprising sulfur and sulfur donor, and polyurethane.

Another aspect is directed to a method for forming an elastomeric article that includes forming a film from a composition comprising a synthetic polyisoprene latex, an accelerator system having a carbamate and a guanidine as the accelerators, a vulcanizing system comprising sulfur and sulfur donor, and polyurethane.

Another aspect is directed to a composition comprising a synthetic polyisoprene latex, an accelerator system comprising a carbamate and a guanidine and a vulcanizing system comprising sulfur, and polyurethane.

Another aspect is directed to a method for forming an elastomeric article that includes forming a film from a composition comprising a synthetic polyisoprene latex, an accelerator system having a carbamate and a guanidine as the accelerators, a vulcanizing system comprising sulfur, and polyurethane.

Another aspect is directed to a composition comprising a synthetic polyisoprene latex, an accelerator system comprising a carbamate, a thiazole and a guanidine and a vulcanizing system comprising sulfur and sulfur donor, and polyurethane.

Another aspect is directed to a method for forming an elastomeric article that includes forming a film from a composition comprising a synthetic polyisoprene latex, an accelerator system having a carbamate, a thiazole and a guanidine as the accelerators, a vulcanizing system comprising sulfur and sulfur donor, and polyurethane.

Another aspect is directed to a composition comprising a synthetic polyisoprene latex, an accelerator system comprising a carbamate, a thiazole and a guanidine and a vulcanizing system comprising sulfur and polyurethane.

Another aspect is directed to a method for forming an elastomeric article that includes forming a film from a composition comprising a synthetic polyisoprene latex, an accelerator system having a carbamate, a thiazole and a guanidine as the accelerator, a vulcanizing system comprising sulfur, and polyurethane.

Another aspect is directed to a composition comprising a synthetic polyisoprene latex, an accelerator system comprising a thiazole and a guanidine and a vulcanizing system comprising sulfur and sulfur donor, and polyurethane.

Another aspect is directed to a method for forming an elastomeric article that includes forming a film from a composition comprising a synthetic polyisoprene latex, an accelerator system having a thiazole and a guanidine as the accelerators, a vulcanizing system comprising sulfur and sulfur donor, and polyurethane.

Another aspect is directed to a composition comprising a synthetic polyisoprene latex, an accelerator system comprising a thiazole and a guanidine and a vulcanizing system comprising sulfur, and polyurethane.

Another aspect is directed to a method for forming an elastomeric article that includes forming a film from a composition comprising a synthetic polyisoprene latex, an accelerator system having a thiazole and a guanidine as the accelerator, a vulcanizing system comprising sulfur, and polyurethane.

Another aspect is directed to a composition comprising a synthetic polyisoprene latex, an accelerator system comprising a guanidine and a vulcanizing system comprising sulfur and sulfur donor, and polyurethane.

Another aspect is directed to a method for forming an elastomeric article that includes forming a film from a composition comprising a synthetic polyisoprene latex, an accelerator system having a guanidine as the accelerator, a vulcanizing system comprising sulfur and sulfur donor, and polyurethane.

Another aspect is directed to a composition comprising a synthetic polyisoprene latex, an accelerator system comprising a guanidine and a vulcanizing system comprising sulfur, and polyurethane.

Another aspect is directed to a method for forming an elastomeric article that includes forming a film from a composition comprising a synthetic polyisoprene latex, an accelerator system having a guanidine as the accelerator, a vulcanizing system comprising sulfur, and polyurethane.

BRIEF DESCRIPTION OF THE DRAWINGS

These and other features, aspects and advantages of the present invention will now be described in connection with preferred embodiments of the invention, in reference to the accompanying drawings. The illustrated embodiments, however, are merely examples and are not intended to limit the invention. The following are brief descriptions of the drawings.

FIG. 1 is an upper plan view of an embodiment of an intermittent urinary catheter assembly according to a preferred embodiment of the present invention.

FIG. 2 is a cross-sectional view through the intermittent urinary catheter assembly from FIG. 1 taken along line 2-2.

DETAILED DESCRIPTION OF THE PREFERRED EMBODIMENTS

Figure 3:
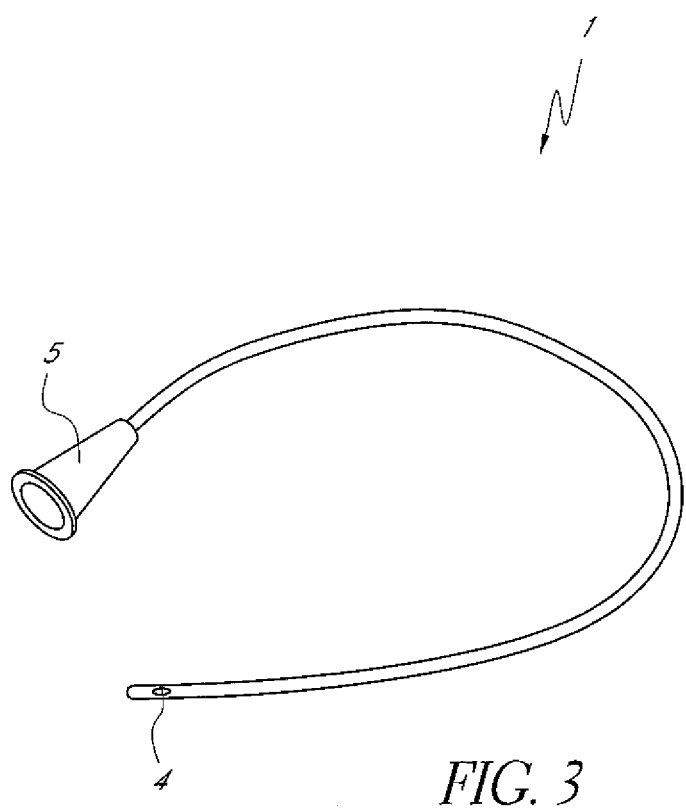
FIG. 3 is a perspective view of the intermittent catheter from FIG. 1, shown removed from the package illustrated in FIG. 1.

The following detailed description is now directed to certain specific embodiments of the invention. In this description, reference is made to the drawings wherein like parts are designated with like numerals throughout the description and the drawings.

Intermittent catheterization typically involves a thin, hollow tube which is threaded through the urinary duct (urethra) and into the bladder to drain urine from the bladder. Conventional intermittent catheters are manufactured from polyvinyl chloride (PVC), or, in some cases, natural rubber latex. PVC is relatively rigid and can cause discomfort for users during and after insertion. Chemical additives can be used to increase the flexibility of PVC; however, these toxic additives can leach into a user's system and cause unwanted reactions.

Natural rubber latex contains proteins that can cause severe allergic reactions in some individuals. Natural rubber latex commonly used in the dipping industries is processed from a sap tapped from *Hevea brasiliensis* trees. Natural rubber latex contains about 1-3% of proteins. About half of these are bound to the surface of the rubber particles to provide the latex stability, and the rest are soluble in the aqueous phase. Proteins from either place are difficult to remove. Natural rubber latex can be centrifuged more than one time and deproteinized substantially to reduce extractable protein from 360 µg/g to 20-50 µg/g. However, even at such low protein levels, some sensitized individuals are still at risk for a Type 1 allergic reaction. In allergic individuals, the levels of IgE antibody to natural rubber latex proteins may be thousands times higher than in those without allergies. For these individuals, exposure even at very low levels can trigger systemic anaphylaxis, local anaphylaxis, hay fever, asthma, and eczema.

Silicone intermittent catheters are sometimes used to avoid toxic and allergic reactions. Silicone catheters, however, require costly tooling and a complex manufacturing process. In addition, they do not have the same feel, physical properties and versatile processing ability as natural rubber latex. For example, silicone does not have the same elastic properties as natural or synthetic polyisoprene rubber. Furthermore, the stiffness of the silicone catheters required for insertion can increase discomfort to the contact tissues after insertion.

Synthetic polyisoprene latex is a man-made polymer that does not contain natural rubber latex or any other proteins (i.e., allergens). In embodiments of the invention, synthetic polyisoprene/polyurethane blends can provide a cost-effective substitute to silicone and a hypoallergenic or non-allergenic alternative to natural rubber latex in forming medical articles, such as intermittent catheters. According to various embodiments, synthetic polyisoprene can be blended with polyurethane to produce intermittent catheters with the feel and physical properties of natural rubber latex without the risk of natural rubber latex allergic reactions to patients and practitioners.

Conventional processes for making elastomeric articles from natural or synthetic latex typically involve preparing a latex dispersion or emulsion, dipping a former in the shape of the article to be manufactured into the latex and curing the latex while on the former. In the curing step, cross-linking or vulcanization through sulfur groups occurs between the polymer units. Certain conventional dipping processes and machinery are applicable to the manufacturing of synthetic polyisoprene catheters. However, conventional compounding formulations and curing conditions used to process natural rubber latex articles may not be adequate to produce synthetic polyisoprene articles having the desired properties for certain medical applications, including use in intermittent catheters.

In embodiments of the invention, an intermittent catheter comprises a blend of polyurethane and synthetic polyisoprene latex (SPIR). Optionally, the catheter may include a hydrophilic outer surface layer. For example, at least a portion of the outer surface layer may include a hydrophilic coating which activates upon exposure to water. The hydrophilic coating provides quick, clean lubrication without the need for external lubricants. The polyurethane/SPIR composition is preferably selected and prepared to be relatively rigid at room temperature and relatively flexible at body temperature, so as to provide a degree of stiffness for insertion of the catheter while reducing discomfort after insertion. Rigidity or stiffness is the property of the medical article to resist deformation. Room temperature may be defined from about 18° C. to about 25° C. A normal range for body temperature is about 36° C. to 38° C. Of course the ranges of room and body temperatures are exemplary and are not limited to the listed values.

Also, in embodiments of the invention, new compounding formulations and processes are provided to achieve the goal of curing synthetic polyisoprene latex and synthetic polyisoprene/polyurethane blends to match the strength of natural rubber latex, while eliminating patient exposure to natural rubber latex protein. Further, in embodiments of the invention, desirable properties of certain elastomeric articles, such as intermittent catheters, can be advantageously influenced or controlled during the compounding, cross-linking and curing stages of the manufacturing process. These properties can include, for example, stiffness, tensile strength, and coefficient of friction.

In preferred embodiments, compounding formulations for synthetic polyisoprene/polyurethane blends are provided, including accelerator systems for synthetic polyisoprene/polyurethane blends and vulcanizing systems for synthetic polyisoprene/polyurethane blends. The accelerator systems can be compounded with the synthetic polyisoprene latex separately from the polyurethane, or after the synthetic polyisoprene is blended with the polyurethane, and can include one or more accelerators. The vulcanizing systems can also be compounded with the synthetic polyisoprene latex separately from the polyurethane, or after the synthetic polyisoprene is blended with the polyurethane, and can include sulfur and one or more sulfur donors. An exemplary accelerator system can include, for example, a combination of a carbamate and a thiazole. An exemplary vulcanizing system can include sulfur and dipentamethylenethiuram hexasulfide (DPTH). Embodiments of the invention also include methods for curing synthetic polyisoprene latex and synthetic polyisoprene/polyurethane blends. The accelerator systems and sulfur curing compounds of embodiments are used to produce synthetic polyisoprene/polyurethane blends having suitable stiffness, at room temperature, for insertion into the body, yet which become softer, and therefore more comfortable, at warmer temperatures (e.g., body temperature).

In the embodiment shown in FIGS. 1 and 2, a urinary drainage catheter 1 is intended for intermittent catheterization of the bladder of a user. The catheter 1 comprises a catheter tube 2 with cross-sectional (e.g., inner diameter and outer diameter) and longitudinal dimensions suitable for introduction of the catheter through the urethra and adequate drainage of the bladder. The catheter tube 2 extends from a distal inlet end 3, in which urine inlet openings 4 are provided, towards a proximal end, at which the catheter tube is connected with an outlet member 5. The outlet member 5 can be configured with a funnel shape, and designed to facilitate the flow of urine from the tube 2. Depending on the patient's capabilities, the outlet member 5 can be configured to flow directly into a toilet, or can be configured to connect the tube 2 with a hose member for transporting urine withdrawn from the bladder to a toilet, into a container, or into a urine collection bag.

The catheter tube 2 comprises a blend of polyurethane and synthetic polyisoprene (SPIR). The polyurethane/SPIR composition is selected and prepared to be relatively rigid at temperatures below body temperature, such as at room temperature, and to become more soft and flexible at body temperature. The polyisoprene/SPIR blend can be manufactured to have any suitable glass transition temperature to achieve this effect and meet the other tensile and resiliency requirements of intermittent applications. Embodiments thus provide an intermittent catheter which is sufficiently rigid to be inserted into the body, while minimizing user discomfort during and after insertion, and while also avoiding unwanted toxic leaching or allergic reactions in sensitive users. Biocompatible polyurethane/SPIR blends can be formulated to have a glass transition temperature in a temperature range of about 20° C. to about 100° C.

In some embodiments, the polyurethane/SPIR blend is configured with a shape memory property, such that the catheter is more easily guided to a specific location upon entry into the body. In some embodiments, a catheter can include portions or sections with different softening temperatures, so as to maintain rigidity in certain portions of the catheter even after insertion, and/or so as to allow for easier guiding of the catheter into a specific location upon entry.

Part or the entire intermittent catheter can comprise the polyurethane/SPIR blend. For example, the tube 2 and/or the distal end 3 can comprise the polyurethane/SPIR blend. The funnel 5 can comprise the same polyurethane/SPIR blend as the tube 2, a different polyurethane/SPIR blend, or a different material altogether. These and other parts can be formed by dip-molding processes, or by extrusion and/or other molding processes, such as injection molding.

On a substantial part of its length from the distal end 3 the catheter tube 2 is, in the illustrated embodiment, coated on its external surface with a lubricious and/or antimicrobial surface coating 6. A suitable lubricious coating 6 includes a hydrophilic surface coating 6. The hydrophilic surface coating 6 can be prepared with a liquid prior to use of the catheter to provide an extremely low friction characteristic of the catheter surface. The low friction characteristic enables the catheter 1 to slide very easily through the urethra while reducing the risk of damaging the urethral walls. A hydrophilic surface layer may, however, be provided by other means and may include a catheter tube of which the active part to be located in the urethra is made entirely of a hydrophilic material. Suitable non-limiting examples of lubricious and antimicrobial coatings are disclosed in U.S. Pat. Nos. 5,459,317; 4,585,666; 5,558,900; 5,077,352; 5,179,174; 6,329,488; 6,716,895; 6,949,598; 7,179,849; and 7,378,156, each of which is incorporated by reference in its entirety.

The catheter 1 may be stored prior to use in a package 7. The package 7 may include, for example, two sheets 8 and 9 of a gas-impermeable thermoplastic film material secured together along a seam 10. The sheets 8, 9 form a cavity 11 surrounding the catheter tube 2. A transition section 13 of the package connects a widened end section 12 to the cavity 11 and preferably follows the external dimensions of the outlet or connector member 5. FIG. 3 shows a perspective view of the catheter 1, removed from the package 7.

Figure 4:
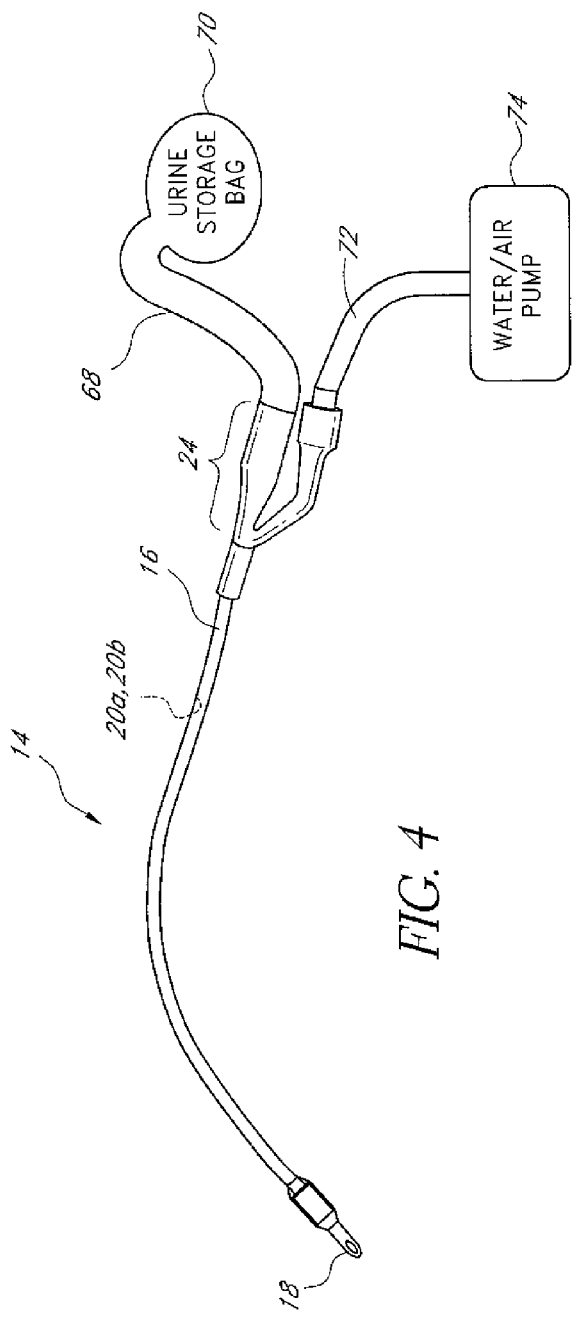
FIG. 4 is a perspective view of an embodiment of a Foley urinary catheter assembly according to a preferred embodiment of the present invention.

FIG. 4 illustrates a catheter 14, such as a Foley urethral catheter, for introduction into a body opening. The catheter 14 may be inserted in the body for a short or long period of time. The catheter 14 includes an elongated flexible body portion 16, which terminates in a tip portion indicated generally at 18. The elongated flexible body portion 16 has a first end and a second end and at least two lumens 20a, 20b. One lumen 20a may be employed for drainage while the other lumen 20b is employed for inflation. As shown, the elongated flexible body portion 16 also has an exterior surface.

The catheter 14 further includes a funnel 24 on its proximal end. At the funnel 24, the lumens 20a, 20b separate. The inflation lumen 20b can connects to a water/air pump 74 through a tube 72. The water/air pump 74 is employed to flow water or air into the inflation lumen 20b.

The drainage lumen 20a passes urine through the funnel 24 and into tube 68. The tube 68 may connect to a urine storage bag 70. While the funnel 24 may be connected to the urine storage bag 70 for an extended period of time, it may only need to be connected to the water/air pump 74 for a long enough period of time to inflate the distal end of the catheter 14 in the bladder.

Figure 5:
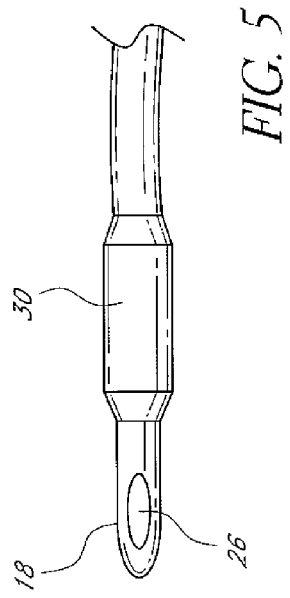
FIG. 5 is a side view of the tip of the Foley catheter from FIG. 4.

FIG. 5 is a side view of a tip 18 of the catheter 14. The tip 18 is typically smaller so as to ease insertion into the meatus opening of the patient. The tip is shown as located on the patient's end of the tube. In the tip 18, a drainage port 26 is shown that allows fluid to enter and exit from the tip. Near the tip 18 is an inflation port 30 which supplies a retaining bag or balloon with air or fluid.

At least a portion of the catheter 14 comprises a blend of polyurethane and synthetic polyisoprene (SPIR). The polyurethane/SPIR composition is selected and prepared to be relatively rigid at temperatures below body temperature, such as at room temperature, and to become more soft and flexible at body temperature. The polyisoprene/SPIR blend can be manufactured to have any suitable glass transition temperature to achieve this effect and meet the other tensile and resiliency requirements of Foley applications. Embodiments thus provide a Foley catheter 14 which is sufficiently rigid to be inserted into the body, while minimizing user discomfort during and after insertion, and while also avoiding unwanted toxic leaching or allergic reactions in sensitive users.

Figure 6:
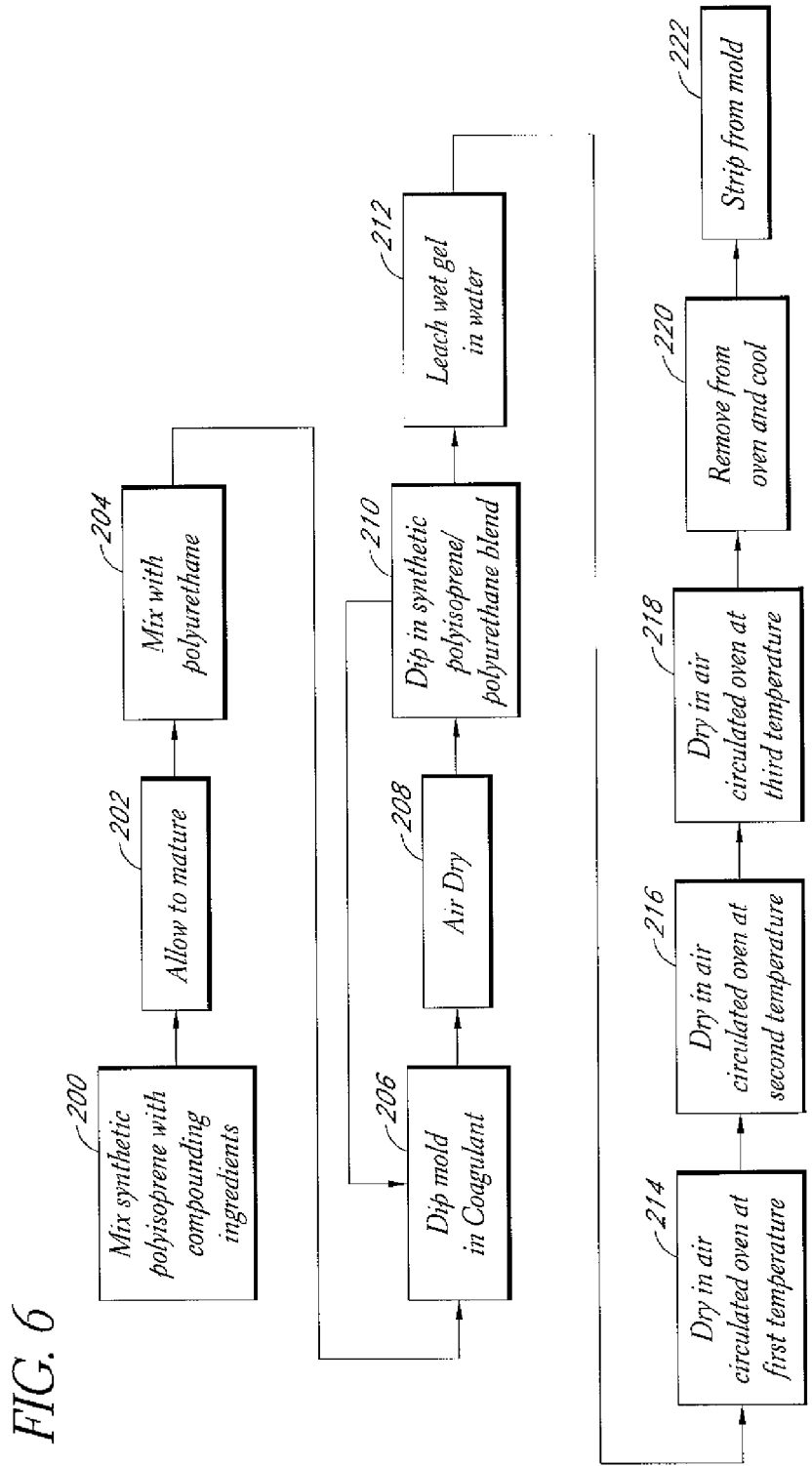
FIG. 6 is a block diagram describing an exemplary process for manufacturing a medical article, such as a Foley catheter or an intermittent catheter, according to a preferred embodiment of the present invention.

In some embodiments, a coagulant dipping process can be used to produce catheters 1, 14 from a synthetic polyisoprene and polyurethane blend. FIG. 6 is a block diagram describing an exemplary process for manufacturing a medical article, such as a Foley catheter 14 or an intermittent catheter 1 according to a preferred embodiment of the present invention. The process begins at step 200 with mixing synthetic polyisoprene with suitable compounding ingredients, including an accelerator system and a curing system. Optionally, at step 202, the mix of synthetic polyisoprene and compounding ingredients can be allowed to mature for a period of time. Maturation can allow compounding ingredients to be absorbed onto the latex particles in colloidal suspension and initiate crosslinking at the outmost surface of the latex particles, which then gradually propagates inward. The period of time can range from several hours to several days. In certain embodiments, the period of time can be at least one day, at least two days, at least three days, or more.

At step 204, the mix can be blended with polyurethane. The amount of polyurethane blended can be selected to achieve the desired material stiffness. In some embodiments, the amount of polyurethane can be about 5% of, 10% of, 20% of, 30% of, 40% of, 50% of, 60% of, 70% of, 80% of, 90% of, 100% (that is, about an equal amount of), or more than the amount of polyisoprene. For example, if 100 parts of synthetic polyisoprene are used, it can be blended with 5, 10, 20, 30, 40, 50, 60, 70, 80, 90, 100, or even more parts of polyurethane. In some embodiments, the blend can include one or more additives, including, for example and without limitation, clay, barium sulfate, calcium carbonate, talc, calcium stearate, magnesium stearate, zinc stearate, polyethylene, a polybutadiene emulsion, a styrene-isoprene-styrene block copolymer emulsion, polyacrylate, polyurethane, polychloroprene, styrene/butadiene copolymer, nitrile latex, zinc oxide (which can also be used as an accelerant), wax, carbon black, silica, titanium dioxide, colored pigments, antioxidants, tackifiers, cellulose, extended oil, and the like. Such additives can be selected to improve physical properties, increase (or decrease) viscosity and hardness and/or decrease the cost of the compounds.

Additives can be obtained from commercial sources. Some examples of commercially available additives include alkylnaphthalene sulfonate as a dispersing agent (for example, 0-0.5 phr of Rhodacal® BX 78, available from Rhodia Inc. of Cranbury, N.J.); paraffin and microcrystalline wax (for example, 0-3 phr of Octowax-5, available from Tiarco Chemical of Dalton, Ga.); hindered phenol (for example, Ti-Nox WL-CF, available from Technical Industries of Peace Dale, R.I.); styrene-maleic anhydride copolymer ammonium salt (for example, 0-1 phr of Impress SC-740, available from Hercules, Inc. of Wilmington, Del.); aluminum silicate (for example, 0-30 phr, available from DuPont); and/or cellulose gum (for example, 0-1 phr of Aqualon CMC-7H$_4$F from Hercules, Inc.).

At step 206, an article-shaped mold can be dipped into a coagulant solution which is capable of destabilizing latex. One example of a suitable coagulant is a solution comprising, for example, 40 gram of calcium nitrate, 8 grams of calcium carbonate and 52 grams of water. At step 208, the dipped mold can be air dried. At step 210, the coagulant-dipped mold can be dipped in the synthetic polyisoprene and polyurethane blend formed at step 204. Optionally, the polyisoprene/polyurethane blend can be heated before the mold is dipped. In step 210, the mold can be dwelled for any suitable length of time, for example 3-20 minutes, preferably 7-12 minutes, in the synthetic polyisoprene and polyurethane blend formed at step 204. The coagulant dip 206, drying step 208, and/or the synthetic polyisoprene/polyurethane dip 210 can be repeated multiple times to build up appropriate thickness required for serving different functionalities of elastomeric articles, as may be desired for a particular application.

Once the desired thickness is achieved, the coagulated wet gel on the mold can be submersed in water at step 212, to leach out the residual compounding ingredients and the coagulant. The leaching process can proceed for up to, or more than, 10 minutes. After the leaching process, the wet gel on the mold can be placed in an oven to dry, for example at a temperature ranging from 50° to 140° C. The drying process can proceed for up to several hours. In some embodiments, as illustrated in FIG. 6, the drying process can proceed in a number of stages, at different temperatures and for different lengths of time. For example, the dipped mold can be dried at step 214 in an air-circulated oven for 10-60 minutes at 55° C., at step 216 for 10-80 minutes at 85° C., and at step 218 for 10-80 minutes at 105° C. The drying times and/or temperatures can be increased, decreased, or both increased and decreased throughout the series of stages. After staying in the oven for the desired length of time, the mold is removed and cooled down at step 220. Finally, at step 222, the elastomeric article is stripped from the mold.

Embodiments of the invention can be provided to the user in a number of ways. For example, embodiments can be packaged dry and configured to be contacted with a wetting fluid after removal from the package. Other embodiments can be packaged with a container of wetting fluid in the package, or can be packaged in a wetting fluid. The various embodiments of catheters described above thus provide a number of advantages over known catheters. Of course, it is to be understood that not necessarily all such objectives or advantages may be achieved in accordance with any particular embodiment of the intermittent catheter described herein. Thus, for example, those skilled in the art will recognize that the catheter may be developed in a manner that achieves or optimizes one advantage or group of advantages as taught herein without necessarily achieving other objectives or advantages as may be taught or suggested herein.

Stereoregular polyisoprene can be synthesized using various catalyst systems to selectively join together monomer units in a well-ordered fashion. The resulting synthetic polyisoprene rubber (SPIR) tends to exceed natural latex rubber in product consistency, cure rate, and purity. SPIR also exhibits superior characteristics in mixing, extrusion, molding, and calendaring processes. Synthetic polyisoprene can be produced by dissolving cis-polyisoprene solid polymer in a solvent, emulsifying the dissolved polymer with surfactants and water, and eventually removing the solvent. An exemplary commercially available synthetic polyisoprene suitable for use with embodiments of the invention includes Kraton IR 401, from Kraton Polymers of Houston, Tex.

In some embodiments, the SPIR can comprise cis-1,4-polyisoprene, trans-1,4-polyisoprene, or can have a primarily 1, 2 or 3, 4 structure. The SPIR can also be crosslinked or otherwise treated to produce the desired characteristics for intermittent catheter applications. Synthetic polyisoprene latex offers several unique features and benefits in the manufacture of intermittent catheters. In addition, the majority of catheter dipping machines are already equipped for aqueous dipping. The use of aqueous latex eliminates the hassle for manufacturers to modify and purchase new machinery and the concerns for environmental control to report and track solvent emission.

Polyurethanes are polymers comprising of a chain of organic units joined by urethane links. Polyurethanes can be formulated to provide good biocompatibility, flexural endurance, high strength and tear resistance, high abrasion resistance and processing versatility. Polyurethane can be produced by reacting isocyanate and polyol in predetermined amounts to achieve desired properties. Some isocyanates that can be used to make polyurethane include diphenylmethane 4,4-diisocyanate, naphthalene 1,5-diisocyanate, toluene diisocyanate, and hexamethylene diisocyanate. Polyols include polyethers and polyesters. Some polyethers have a relatively low molecular weight, for example in the range of 500 to 3000, and are manufactured from propylene and ethylene oxide. Polyester polyols can be produced by reacting a diol with dicarboxylic acid. Polyurethane polymers include both hard and soft segments. At colder temperatures, the hard segments align together in clusters and act as "pseudo crosslinks," allowing the polyurethane to behave as an elastomer for achieving elasticity. However, when the temperature is raised these clusters can dissociate and slide away, rendering the polyurethane softer. An exemplary commercially available polyurethane suitable for use with embodiments of the invention includes AMPUD-12A from Ortec, Inc. of Easley, S.C.

In some embodiments, the manufacturing process used to produce elastomeric articles, such as Foley catheters or intermittent catheters, can also involve a curing step which crosslinks or vulcanizes polymer units into a three-dimensional network. Sulfur can be used in combination with one or more accelerators to initiate and propagate crosslinks. Sulfur forms ring and chain structures. In the crosslinking process, the 8-membered sulfur ring splits into shorter chain structure and links individual polymers together to form thermoset materials. Various accelerators can be used to speed up the formation of the sulfur short chain structure. The number of sulfur atoms in the sulfur bridges alters the physical properties of the materials. Short bridges containing only one or two sulfur atoms offer heat resistance, for example, and long bridges offer flexibility. In addition, using sulfur bearing compounds (i.e., a sulfur donor) instead of, or in addition to sulfur can increase resistance of rubber articles to heat exposure. Possible sulfur donors that can be used with embodiments of the invention include tetrabutylthiuram disulfide, tetraethylthiuram disulfide, tetramethylthiuram disulfide, dipentamethylenethiuram hexasulfide, and tetramethylthiuram monosulfide. Some commercially available sources of sulfur and sulfur donors include Ti-rite S-4 and Ti-Cure SF-CF dipentamethylenethiuram hexasulfide (Sulfads), available from available from Technical Industries of Peace Dale, R.I.

Accelerator systems according to embodiments of the invention can include, for example, carbamates, thiazoles, and/or guanidines. These accelerators can be used alone or a combination with other accelerators. Suitable dithiocarbamates include, for example, bismuth dimethyldithiocarbamate, cadmium diethyl dithiocarbamate, copper dimethyl dithiocarbamate, sodium dimethyl dithiocarbamate, sodium dibutyl dithiocarbamate, zinc dimethyl dithiocarbamate, zinc diethyl dithiocarbamate, zinc dibutyl dithiocarbamate, zinc dipentamethylene dithiocarbamate, zinc diisobutyldithiocarbamate, zinc diamyldithiocarbamate, piperidinium pentamethylenedithiocarbamate, zinc dibenzyl dithiocarbamate, and zinc ethyl phenyl dithiocarbamate. Suitable thiazoles include, for example, benzothiazyl disulfide, 2-mercaptobenzothiazole, zinc mercaptobenzothiazole, and 2-(2',4'-dinitrophenylthio) benothiazole. Suitable guanidines include, for example, N,N'-di-ortho-tolyguanidine, N,N'-diphenylguanidine, and Di-ortho-tolylguanidine. Some examples of commercially available accelerants include Octocure ZMBT-50 and Octocure ZDB-50, available from Tiarco Chemical of Dalton, Ga., and Ti-rite Zn-B, available from Technical Industries of Peace Dale, R.I.

Sulfur-curing systems according to embodiments of the invention can employ a high ratio of sulfur to accelerators, or a low ratio of sulfur to accelerators. When a low sulfur/accelerator ratio is used, more mono-sulfidic than polysulfidic bonds are present in crosslinks. Either method can be used to produce elastomeric articles with desirable properties for a particular application.

The several examples set forth below demonstrate material properties that can be obtained and influenced with synthetic polyisoprene/polyurethane blends, according to embodiments of the invention. Examples 1-43 illustrate suitable synthetic polyisoprene compounding formulations for use with embodiments of the invention, and demonstrate that carbamate or guanidine alone or a combination of carbamate and guanidine or a combination of carbamate and thiazole or a combination of carbamate, guanidine and thiazole can produce rubber articles having a tensile strength greater than, for example, 3000 psi. Sulfur or a combination of sulfur and a sulfur donor, in a total amount ranging from 1.0 phr to 4.5 phr, are used to adjust curing and heat resistance. Potassium hydroxide or ammonium hydroxide can be used to adjust the pH of the compounded latex. Examples 44-49 show that adding polyurethane to synthetic polyisoprene formulations can increase the stiffness of catheters to facilitate insertion. Examples 50 and 51 below show that synthetic polyisoprene/polyurethane blends can be formulated which become soft when they enter the body, thereby providing some relief to patients from the pressure of a hard catheter.

In the examples below, modulus at 300% or 500% is performed by Instron 5564 and measured according to ASTM D412. Young's modulus is used to measure the stiffness of catheters. When a material is subjected to an external stress it becomes distorted or strained. The ratio of the linear stress to the linear strain is termed the modulus of elasticity, more commonly known as Young's modulus. The 300% modulus is Young's modulus when a specimen is elongated to 300% of its original length. The 500% modulus is measured the modulus at 500% of elongation. A higher modulus indicates that the material is stiffer than one with a lower modulus.

EXAMPLE 1

Synthetic polyisoprene latex is compounded with the ingredients listed below, and used to produce dip-molded articles. The articles are cured for 30 minutes at 55° C., 45 minutes at 105° C., and 20 minutes at 115° C. The articles exhibit the following physical properties: tensile strength of 3421 psi, elongation at break of 1113%, and 500% modulus of 206 psi.

TABLE 1

| Compounding Ingredients | Parts per hundred rubber |
| --- | --- |
| Synthetic polyisoprene latex | 100 |
| Potassium hydroxide | 0.2 |
| Sulfur or sulfur donor or a combination | 1-4 |
| Sulfur | 2.0 |
| Sulfur donor | 1.0 |
| Sodium dibutyl dithiocarbamate | 0.025 |
| Zinc oxide | 1.5 |
| Hindered phenol | 2.0 |

EXAMPLE 2

Synthetic polyisoprene latex is compounded with the ingredients listed below, and used to produce dip-molded articles. The articles are cured for 30 minutes at 55° C., 45 minutes at 105° C., and 20 minutes at 115° C. The articles exhibit the following physical properties: tensile strength of 3393 psi, elongation at break of 1138%, and 500% modulus of 268 psi.

| 2. Compounding Ingredients | Parts per hundred rubber |
| --- | --- |
| Synthetic polyisoprene latex | 100 |
| Potassium hydroxide | 0.2 |
| Sulfur or sulfur donor or a combination | 1-4 |
| Sulfur | 2.0 |
| Sulfur donor | 1.0 |
| Diphenylguanidine | 0.5 |
| Zinc oxide | 1.5 |
| Hindered phenol | 2.0 |

EXAMPLE 3

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3191 psi, elongation at break of 1025%, and 500% modulus of 267 psi.

| 3. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.0 |
| Sulfur donor | 0.5 |
| Sodium dibutyl dithiocarbamate | 0.1 |
| Zinc oxide | 1.5 |
| Hindered phenol | 1.0 |

EXAMPLE 4

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3122 psi, elongation at break of 756%, and 500% modulus of 586 psi.

| 4. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Sulfur donor | 1.5 |
| Diphenylguanidine | 0.25 |
| Sodium dibutyl dithiocarbamate | 0.1 |
| Zinc mercaptobenzothiazole | 0.5 |
| Zinc oxide | 1.5 |
| Hindered phenol | 1.0 |

EXAMPLE 5

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3383 psi, elongation at break of 900%, and 500% modulus of 326 psi.

| 5. Compounding Ingredients | Parts per hundred rubber |
|---|---|
| Synthetic polyisoprene latex | 100 |
| Sulfur or sulfur donor or a combination | 1-4 |
| Sulfur | 2.0 |
| Sulfur donor | 1.0 |
| Sodium dibutyl dithiocarbamate | 0.1 |
| Zinc mercaptobenzothiazole | 0.5 |
| Zinc oxide | 1.5 |
| Hindered phenol | 1.0 |

EXAMPLE 6

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3173 psi, elongation at break of 908%, and 500% modulus of 312 psi.

| 6. Compounding Ingredients | Parts per hundred rubber |
|---|---|
| Synthetic polyisoprene latex | 100 |
| Sulfur or sulfur donor or a combination | 1-4 |
| Sulfur | 2.0 |
| Sulfur donor | 1.0 |
| Sodium dibutyl dithiocarbamate | 0.1 |
| Zinc mercaptobenzothiazole | 1.0 |
| Zinc oxide | 1.5 |
| Hindered phenol | 1.0 |

EXAMPLE 7

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3240 psi, elongation at break of 1044%, and 500% modulus of 229 psi.

| 7. Compounding Ingredients | Parts per hundred rubber |
|---|---|
| Synthetic polyisoprene latex | 100 |
| Potassium hydroxide | 0.05 |
| Sulfur or sulfur donor or a combination | 1-4 |
| Sulfur | 1.5 |
| Sulfur donor | 1.5 |
| Sodium dibutyl dithiocarbamate | 0.1 |
| Zinc oxide | 1.5 |
| Hindered phenol | 1.0 |

EXAMPLE 8

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3456 psi, elongation at break of 971%, and 500% modulus of 294 psi.

TABLE 8

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2 |
| Sulfur donor | 1 |
| Diphenylguanidine | 0.25 |
| Sodium dibutyl dithiocarbamate | 0.1 |
| Zinc oxide | 1.5 |
| Hindered phenol | 1.0 |

EXAMPLE 9

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3246 psi, elongation at break of 878%, and 500% modulus of 347 psi.

TABLE 9

| Compounding Ingredients | Parts per hundred rubber |
| --- | --- |
| Synthetic polyisoprene latex | 100 |
| Potassium hydroxide | 0.1 |
| Sulfur or sulfur donor or a combination | 1-4 |
| Sulfur | 2 |
| Sulfur donor | 1 |
| Zinc mercaptobenzothiazole | 0.5 |
| Sodium dibutyl dithiocarbamate | 0.1 |
| Zinc oxide | 1.5 |
| Hindered phenol | 1.0 |

EXAMPLE 10

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3920 psi, elongation at break of 875%, and 500% modulus of 465 psi.

| 10. Compounding Ingredients | Parts per hundred rubber |
| --- | --- |
| Synthetic polyisoprene latex | 100 |
| Ammonium hydroxide | 0.2 |
| Sulfur or sulfur donor or a combination | 1-4 |
| Sulfur | 2 |
| Sulfur donor | 1 |
| Zinc mercaptobenzothiazole | 0.5 |
| Sodium dibutyl dithiocarbamate | 0.1 |
| Zinc oxide | 1.5 |
| Hindered phenol | 0.5 |

EXAMPLE 11

Synthetic polyisoprene latex was prepared with the compounding ingredients listed and then Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3291 psi, elongation at break of 858%, and 500% modulus of 405 psi.

| 11. Compounding Ingredients | Parts per hundred rubber |
| --- | --- |
| Synthetic polyisoprene latex | 100 |
| Ammonium hydroxide | 0.2 |
| Sulfur or sulfur donor or a combination | 1-4 |
| Sulfur | 2 |
| Sulfur donor | 1 |
| Zinc mercaptobenzothiazole | 0.5 |
| Sodium dibutyl dithiocarbamate | 0.1 |
| Zinc oxide | 0.5 |
| Hindered phenol | 0.5 |

EXAMPLE 12

Synthetic polyisoprene latex is compounded with the ingredients listed below, and used to produce dip-molded articles. The articles are cured 30 minutes at 55° C. and 45 minutes at 115° C. The articles exhibit the following physical properties: tensile strength of 3124 psi, elongation at break of 905%, and 500% modulus of 346 psi.

| 12. Compounding Ingredients | Parts per hundred rubber |
| --- | --- |
| Synthetic polyisoprene latex | 100 |
| Potassium hydroxide | 0.1 |
| Ammonium hydroxide | 0.2 |
| Sulfur or sulfur donor or a combination | 1-4 |
| Sulfur | 2 |
| Sulfur donor | 1 |
| Zinc mercaptobenzothiazole | 0.5 |
| Sodium dibutyl dithiocarbamate | 0.1 |
| Zinc oxide | 0.5 |
| Hindered phenol | 0.5 |

EXAMPLE 13

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3530 psi, elongation at break of 1017%, and 500% modulus of 255 psi.

| 13. Compounding Ingredients | Parts per hundred rubber |
| --- | --- |
| Synthetic polyisoprene latex | 100 |
| Potassium hydroxide | 0.1 |
| Ammonium hydroxide | 0.2 |
| Sulfur or sulfur donor or a combination | 1-4 |
| Sulfur | 2 |
| Sulfur donor | 1 |
| Sodium dibutyl dithiocarbamate | 0.1 |
| Zinc oxide | 0.5 |
| Hindered phenol | 0.5 |

EXAMPLE 14

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3582 psi, elongation at break of 1063%, and 500% modulus of 249 psi.

| 14. Compounding Ingredients | Parts per hundred rubber |
| --- | --- |
| Synthetic polyisoprene latex | 100 |
| Potassium hydroxide | 0.2 |
| Sulfur or sulfur donor or a combination | 1-4 |
| Sulfur | 2 |
| Sulfur donor | 1 |
| Zinc dibutyl dithiocarbamate | 0.1 |
| Zinc oxide | 0.5 |
| Hindered phenol | 0.5 |

EXAMPLE 15

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3316 psi, elongation at break of 1069%, and 500% modulus of 231 psi.

| 15. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2 |
| Sulfur donor | 1 |
| Diphenylguanidine | 0.5 |
| Zinc diethyl dithiocarbamate | 0.1 |
| Zinc oxide | 0.5 |
| Hindered phenol | 0.5 |

EXAMPLE 16

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3506 psi, elongation at break of 1109%, and 500% modulus of 221 psi.

| 16. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Sulfur donor | 0.5 |
| Zinc mercaptobenzothiazole | 0.5 |
| Zinc diethyl dithiocarbamate | 0.25 |
| Zinc oxide | 0.5 |
| Hindered phenol | 0.5 |

EXAMPLE 17

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3609 psi, elongation at break of 1100%, and 500% modulus of 231 psi.

| 17. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Zinc mercaptobenzothiazole | 0.5 |
| Zinc diethyl dithiocarbamate | 0.25 |
| Zinc oxide | 0.5 |
| Hindered phenol | 0.5 |

EXAMPLE 18

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3805 psi, elongation at break of 1100%, and 500% modulus of 321 psi.

| 18. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Sulfur donor | 0.5 |
| Diphenylguanidine | 0.5 |
| Zinc dipentamethylene dithiocarbamate | 0.25 |
| Zinc oxide | 0.5 |
| Hindered phenol | 0.5 |

EXAMPLE 19

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3706 psi, elongation at break of 1000%, and 500% modulus of 235 psi.

| 19. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Diphenylguanidine | 0.5 |
| Zinc dipentamethylene dithiocarbamate | 0.25 |
| Zinc oxide | 0.5 |
| Hindered phenol | 0.5 |

EXAMPLE 20

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3073 psi, elongation at break of 1000%, and 500% modulus of 161 psi.

| 20. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2 |
| Sulfur donor | 1 |
| Diphenylguanidine | 0.5 |
| Zinc dipentamethylene dithiocarbamate | 0.1 |
| Zinc oxide | 0.5 |
| Hindered phenol | 0.5 |

EXAMPLE 21

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3179 psi, elongation at break of 1050%, and 500% modulus of 251 psi.

| 21. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2 |
| Sulfur donor | 1 |
| Zinc mercaptobenzothiazole | 0.5 |
| Zinc dipentamethylene dithiocarbamate | 0.25 |
| Zinc oxide | 0.5 |
| Hindered phenol | 0.5 |

EXAMPLE 22

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3002 psi, elongation at break of 1020%, and 500% modulus of 261 psi.

| 22. Compounding Ingredients | Parts per hundred rubber |
|---|---|
| Synthetic polyisoprene latex | 100 |
| Sulfur or sulfur donor or a combination | 1-4 |
| Sulfur | 1 |
| Diphenylguanidine | 0.5 |
| Zinc dipentamethylene dithiocarbamate | 0.25 |
| Zinc oxide | 0.5 |
| Hindered phenol | 0.5 |

EXAMPLE 23

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3338 psi, elongation at break of 950%, and 500% modulus of 285 psi.

| 23. Compounding Ingredients | Parts per hundred rubber |
|---|---|
| Synthetic polyisoprene latex | 100 |
| Sulfur or sulfur donor or a combination | 1-4 |
| Sulfur | 1 |
| Zinc mercaptobenzothiazole | 0.5 |
| Zinc dipentamethylene dithiocarbamate | 0.25 |
| Zinc oxide | 0.5 |
| Hindered phenol | 0.5 |

EXAMPLE 24

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3315 psi, elongation at break of 1080%, and 500% modulus of 285 psi.

| 24. Compounding Ingredients | Parts per hundred rubber |
|---|---|
| Synthetic polyisoprene latex | 100 |
| Sulfur or sulfur donor or a combination | 1-4 |
| Sulfur | 1 |
| Diphenylguanidine | 0.5 |
| Zinc dibutyl dithiocarbamate | 0.15 |
| Zinc oxide | 0.5 |
| Hindered phenol | 0.5 |

EXAMPLE 25

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3377 psi, elongation at break of 1100%, and 500% modulus of 237 psi.

| 25. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 1 |
| Sulfur donor | 0.25 |
| Zinc mercaptobenzothiazole | 0.5 |
| Zinc dibutyl dithiocarbamate | 0.15 |
| Zinc oxide | 0.5 |
| Hindered phenol | 0.5 |

EXAMPLE 26

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3315 psi, elongation at break of 1080%, and 500% modulus of 261 psi.

| 26. Compounding Ingredients | Parts per hundred rubber |
|---|---|
| Synthetic polyisoprene latex | 100 |
| Sulfur or sulfur donor or a combination | 1-4 |
| Sulfur | 1 |
| Sulfur donor | 0.25 |
| Diphenylguanidine | 0.5 |
| Zinc dipentamethylene dithiocarbamate | 0.25 |
| Zinc oxide | 0.5 |
| Hindered phenol | 0.5 |

EXAMPLE 27

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3869 psi, elongation at break of 1100%, and 500% modulus of 231 psi.

| 27. Compounding Ingredients | Parts per hundred rubber |
|---|---|
| Synthetic polyisoprene latex | 100 |
| Sulfur or sulfur donor or a combination | 1-4 |
| Sulfur | 1 |
| Sulfur donor | 0.25 |
| Zinc mercaptobenzothiazole | 0.5 |

-continued

| 27. Compounding Ingredients | Parts per hundred rubber |
|---|---|
| Zinc dipentamethylene dithiocarbamate | 0.25 |
| Zinc oxide | 0.5 |
| Hindered phenol | 0.5 |

EXAMPLE 28

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3376 psi, elongation at break of 1100%, and 500% modulus of 237 psi.

| 28. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1 |
| Sulfur donor | 0.25 |
| Diphenylguanidine | 0.5 |
| Zinc dibutyl dithiocarbamate | 0.15 |
| Zinc oxide | 0.5 |
| Hindered phenol | 0.5 |

EXAMPLE 29

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3579 psi, elongation at break of 1000%, and 500% modulus of 242 psi.

| 29. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1 |
| Sulfur donor | 0.25 |
| Zinc mercaptobenzothiazole | 0.5 |
| Zinc dibutyl dithiocarbamate | 0.15 |
| Zinc oxide | 0.5 |
| Hindered phenol | 0.5 |

EXAMPLE 30

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3384 psi, elongation at break of 810%, and 500% modulus of 470 psi.

| 30. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.5 |

-continued

| 30. Compounding Ingredients | Parts per hundred rubber |
|---|---|
| Sulfur donor | 1.5 |
| Zinc dibenzyl dithiocarbamate | 0.5 |
| Zinc oxide | 0.5 |
| Hindered phenol | 0.5 |

EXAMPLE 31

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3805 psi, elongation at break of 820%, and 500% modulus of 454 psi.

| 31. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.5 |
| Sulfur donor | 1.5 |
| Diphenylguanidine | 0.5 |
| Zinc oxide | 0.5 |
| Hindered phenol | 0.5 |

EXAMPLE 32

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3383 psi, elongation at break of 810%, and 500% modulus of 470 psi.

| 32. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.5 |
| Sulfur donor | 1.5 |
| Zinc mercaptobenzothiazole | 0.5 |
| Zinc dibutyl dithiocarbamate | 0.1 |
| Zinc oxide | 0.5 |
| Hindered phenol | 0.5 |

EXAMPLE 33

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3767 psi, elongation at break of 875%, and 500% modulus of 393 psi.

| 33. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.5 |

| 33. Compounding Ingredients | Parts per hundred rubber |
|---|---|
| Sulfur donor | 1.5 |
| Zinc mercaptobenzothiazole | 0.5 |
| Zinc diethyl dithiocarbamate | 0.25 |
| Zinc oxide | 2.0 |
| Hindered phenol | 2.0 |

EXAMPLE 34

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3630 psi, elongation at break of 890%, and 500% modulus of 396 psi.

| 34. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.5 |
| Sulfur donor | 1.5 |
| Diphenylguanidine | 0.5 |
| Zinc dibutyl dithiocarbamate | 0.1 |
| Zinc oxide | 2.0 |
| Hindered phenol | 2.0 |

EXAMPLE 35

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3438 psi, elongation at break of 890%, and 500% modulus of 394 psi.

| 35. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.5 |
| Sulfur donor | 1.5 |
| Diphenylguanidine | 0.5 |
| Zinc diethyl dithiocarbamate | 0.1 |
| Zinc oxide | 2.0 |
| Hindered phenol | 2.0 |

EXAMPLE 36

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3291 psi, elongation at break of 858%, and 500% modulus of 405 psi.

| 36. Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 2.5 |
| Sulfur donor | 1.5 |
| Diphenylguanidine | 0.5 |
| Zinc dimethyl dithiocarbamate | 0.2 |
| Zinc oxide | 2.0 |
| Hindered phenol | 2.0 |

EXAMPLE 37

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3241 psi, elongation at break of 1040%, and 500% modulus of 188 psi.

| 37. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 2.5 |
| Sulfur donor | 0.25 |
| Zinc dibenzyl dithiocarbamate | 0.5 |
| Zinc oxide | 2.0 |
| Hindered phenol | 2.0 |

EXAMPLE 38

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3198 psi, elongation at break of 900%, and 500% modulus of 203 psi.

| 38. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 2.5 |
| Sulfur donor | 0.25 |
| Sodium dibutyl dithiocarbamate | 0.1 |
| Zinc oxide | 2.0 |
| Hindered phenol | 2.0 |

EXAMPLE 39

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3475 psi, elongation at break of 1020%, and 500% modulus of 157 psi.

| 39. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 2.5 |
| Sulfur donor | 0.25 |
| Diphenylguanidine | 0.5 |
| Zinc oxide | 2.0 |
| Hindered phenol | 2.0 |

EXAMPLE 40

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3651 psi, elongation at break of 1010%, and 500% modulus of 158 psi.

| 40. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 2.5 |
| Sulfur donor | 0.25 |
| Zinc mercaptobenzothiazole | 0.5 |
| Zinc dibutyl dithiocarbamate | 0.1 |
| Zinc oxide | 2.0 |
| Hindered phenol | 2.0 |

EXAMPLE 41

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3623 psi, elongation at break of 975%, and 500% modulus of 158 psi.

| 41. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 2.5 |
| Sulfur donor | 0.25 |
| Zinc mercaptobenzothiazole | 0.5 |
| Zinc diethyl dithiocarbamate | 0.25 |
| Zinc oxide | 0.5 |
| Hindered phenol | 0.5 |

EXAMPLE 42

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3770 psi, elongation at break of 1080%, and 500% modulus of 296 psi.

| 42. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 2.5 |
| Sulfur donor | 0.25 |
| Diphenylguanidine | 0.5 |
| Zinc dibutyl dithiocarbamate | 0.1 |
| Zinc oxide | 0.5 |
| Hindered phenol | 0.5 |

EXAMPLE 43

Synthetic polyisoprene latex is compounded with the ingredients listed below, and used to produce dip-molded articles. The articles are cured for 30 minutes at 55° C. and 45 minutes at 115° C. The articles exhibit the following physical properties: tensile strength of 3476 psi, elongation at break of 950%, and 500% modulus of 305 psi.

| 43. Compounding Ingredients | Parts per hundred rubber |
|---|---|
| Synthetic polyisoprene latex | 100 |
| Ammonium hydroxide | 0.1 |
| Sulfur or sulfur donor or a combination | 1-4 |
| Sulfur | 2.5 |
| Sulfur donor | 0.25 |
| Diphenylguanidine | 0.5 |
| Zinc dimethyl dithiocarbamate | 0.1 |
| Zinc oxide | 0.5 |
| Hindered phenol | 0.5 |

Additional exemplary synthetic polyisoprene compounding formulations for use in step 200 of FIG. 6, including various accelerator and curing systems, are set forth below in Tables 44-56. Each compound of synthetic latex includes an accelerator system and a curing system. The compounds listed below are exemplary and should not be construed as limiting the claims to the embodiments depicted therein. For example, any of the accelerators can be used with any of the curing compounds listed below. Further, the amounts of the accelerators and curing compounds listed in the examples below can be varied (increased or decreased, relative to or together with other accelerator(s) and curing compound(s)) to produce different material properties. In addition, different compounds can be used for different layers of a multi-layer medical article, or for different portions of a medical article.

TABLE 44

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Sulfur donor | 0.5 |
| Diphenylguanidine | 0.5 |
| Zinc oxide | 1.5 |
| Hindered phenol | 2.0 |

TABLE 45

| Compounding Ingredients | Parts per hundred rubber |
|---|---|
| Synthetic polyisoprene latex | 100 |
| Potassium hydroxide | 0.1 |
| Sulfur or sulfur donor or a combination | 1-4 |
| Sulfur | 1.5 |
| Sodium dibutyl dithiocarbamate | 0.1 |
| Zinc oxide | 1.5 |
| Hindered phenol | 1.0 |

TABLE 46

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Sulfur donor | 0.5 |
| Diphenylguanidine | 0.25 |
| Sodium dibutyl dithiocarbamate | 0.1 |
| Zinc mercaptobenzothiazole | 0.5 |
| Zinc oxide | 1.5 |
| Hindered phenol | 1.0 |

TABLE 47

| Compounding Ingredients | Parts per hundred rubber |
|---|---|
| Synthetic polyisoprene latex | 100 |
| Sulfur or sulfur donor or a combination | 1-4 |
| Sulfur | 2.0 |
| Sodium dibutyl dithiocarbamate | 0.1 |
| Zinc mercaptobenzothiazole | 0.5 |
| Zinc oxide | 1.5 |
| Hindered phenol | 1.0 |

TABLE 48

| Compounding Ingredients | Parts per hundred rubber |
|---|---|
| Synthetic polyisoprene latex | 100 |
| Sulfur or sulfur donor or a combination | 1-4 |
| Sulfur | 1.5 |
| Sulfur donor | 0.5 |
| Zinc diethyl dithiocarbamate | 0.25 |
| Zinc mercaptobenzothiazole | 1.0 |
| Zinc oxide | 1.5 |
| Hindered phenol | 1.0 |

TABLE 49

| Compounding Ingredients | Parts per hundred rubber |
|---|---|
| Synthetic polyisoprene latex | 100 |
| Potassium hydroxide | 0.05 |
| Sulfur or sulfur donor or a combination | 1-4 |
| Sulfur | 1.5 |
| Sulfur donor | 1.5 |
| Zinc dibutyl dithiocarbamate | 0.1 |
| Zinc oxide | 1.5 |
| Hindered phenol | 1.0 |

TABLE 50

| Compounding Ingredients | Parts per hundred rubber |
|---|---|
| Synthetic polyisoprene latex | 100 |
| Ammonium hydroxide | 0.2 |
| Sulfur or sulfur donor or a combination | 1-4 |
| Sulfur | 1.5 |
| Zinc mercaptobenzothiazole | 0.5 |
| Sodium dibutyl dithiocarbamate | 0.1 |
| Zinc oxide | 1.5 |
| Hindered phenol | 0.5 |

TABLE 51

| Compounding Ingredients | Parts per hundred rubber |
|---|---|
| Synthetic polyisoprene latex | 100 |
| Ammonium hydroxide | 0.2 |
| Sulfur or sulfur donor or a combination | 1-4 |
| Sulfur | 1.5 |
| Sulfur donor | 0.5 |
| Zinc mercaptobenzothiazole | 0.5 |
| Sodium dibutyl dithiocarbamate | 0.1 |
| Zinc oxide | 0.5 |
| Hindered phenol | 0.5 |

TABLE 52

| Compounding Ingredients | Parts per hundred rubber |
|---|---|
| Synthetic polyisoprene latex | 100 |
| Potassium hydroxide | 0.1 |
| Ammonium hydroxide | 0.2 |
| Sulfur or sulfur donor or a combination | 1-4 |
| Sulfur | 2 |
| Sulfur donor | 1 |
| Zinc mercaptobenzothiazole | 0.5 |
| Zinc dipentamethylene dithiocarbamate | 0.25 |
| Zinc oxide | 0.5 |
| Hindered phenol | 0.5 |

TABLE 53

| Compounding Ingredients | Parts per hundred rubber |
|---|---|
| Synthetic polyisoprene latex | 100 |
| Potassium hydroxide | 0.1 |
| Ammonium hydroxide | 0.2 |
| Sulfur or sulfur donor or a combination | 1-4 |
| Sulfur | 1.5 |
| Sulfur donor | 0.5 |
| Zinc mercaptobenzothiazole | 0.5 |
| Zinc dipentamethylene dithiocarbamate | 0.25 |
| Zinc oxide | 0.5 |
| Hindered phenol | 0.5 |

TABLE 54

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Sulfur | 1.5 |
| Zinc mercaptobenzothiazole | 0.5 |
| Zinc dipentamethylene dithiocarbamate | 0.25 |
| Zinc oxide | 0.5 |
| Hindered phenol | 0.5 |

TABLE 55

| Compounding Ingredients | Parts per hundred rubber |
| --- | --- |
| Synthetic polyisoprene latex | 100 |
| Potassium hydroxide | 0.2 |
| Sulfur or sulfur donor or a combination | 1-4 |
| Sulfur | 2 |
| Sulfur donor | 1 |
| Diphenylguanidine | 0.5 |
| Zinc dipentamethylene dithiocarbamate | 0.2 |
| Zinc oxide | 0.5 |
| Hindered phenol | 0.5 |

TABLE 56

| Compounding Ingredients | Parts per hundred rubber |
| --- | --- |
| Synthetic polyisoprene latex | 100 |
| Potassium hydroxide | 0-0.5 |
| Sulfur or sulfur donor or a combination | 1-4.5 |
| Sulfur | 1-3 |
| Sulfur donor | 0-1.5 |
| Zinc mercaptobenzothiazole | 0-1 |
| Zinc dibutyl dithiocarbamate | 0.01-1 |
| Zinc oxide | 0.01-3 |
| Hindered phenol | 0-3 |

EXAMPLE 44

A water-based aliphatic polyisoprene dispersion, Bayhydrol® PR 110 (available from Bayer MaterialScience), is blended with 5 and 10% (of the amount of polyisoprene) of polyurethane. The resulting 500% modulus for the different blends is shown in Table 57 below.

TABLE 57

| | Percent of Polyurethane Added | | |
| --- | --- | --- | --- |
| | 0 | 5 | 10 |
| 500% Modulus, psi | 258 | 681 | 920 |

Table 57 shows that adding 5% of polyurethane can increase the 500% modulus of a particular formulation from 258 psi to 681 psi. The stiffness of catheters formed using this formulation can be thus increased about 164 percent. Adding 10% of polyurethane can increase the 500% modulus of a particular formulation from 258 psi to 920 psi. The stiffness of catheters can thus be increased about 250 percent.

EXAMPLE 45

Another water-based aliphatic polyisoprene dispersion, Bayhydrol® PR 240 (available from Bayer MaterialScience), is blended with 5 and 10% (of the amount of polyisoprene) of polyurethane. The resulting 500% modulus for the different blends is shown in Table 58 below.

TABLE 58

| | Percent of Polyurethane Added | | |
| --- | --- | --- | --- |
| | 0 | 5 | 10 |
| 500% Modulus, psi | 258 | 436 | 592 |

Table 58 shows that adding 5% of polyurethane can increase the 500% modulus of a particular formulation from 258 psi to 436 psi. The stiffness of catheters formed using this formulation can be thus increased about 69 percent. Adding 10% of polyurethane can increase the 500% modulus of a particular formulation from 258 psi to 592 psi. The stiffness of catheters can thus be increased about 125 percent.

EXAMPLE 46

Still another water-based aliphatic polyisoprene dispersion, AMPUD-10 (from Ortec, Inc.), is blended with 5 and 10% (of the amount of polyisoprene) of polyurethane. The resulting 500% modulus for the different blends is shown in Table 59 below.

TABLE 59

| | Percent of Polyurethane Added | | |
| --- | --- | --- | --- |
| | 0 | 5 | 10 |
| 500% Modulus, psi | 282 | 736 | 1086 |

Table 59 shows that adding 5% of polyurethane can increase the 500% modulus of a particular formulation from 282 psi to 736 psi. The stiffness of catheters formed using this formulation can be thus increased about 161 percent. Adding 10% of polyurethane can increase the 500% modulus of a particular formulation from 282 psi to 1086 psi. The stiffness of catheters can thus be increased about 280 percent.

EXAMPLE 47

A water-based aliphatic polyisoprene dispersion, AMPUD-10 (from Ortec, Inc.), is blended with 5 and 10% (of the amount of polyisoprene) of polyurethane. The resulting 500% modulus for the different blends is shown in Table 60 below.

TABLE 60

| | Percent of Polyurethane Added | | |
| --- | --- | --- | --- |
| | 0 | 5 | 10 |
| 500% Modulus, psi | 310 | 510 | 780 |

Table 60 shows that adding 5% of polyurethane can increase the 500% modulus of a particular formulation from 310 psi to 510 psi. The stiffness of catheters formed using this formulation can be thus increased about 65 percent. Adding 10% of polyurethane can increase the 500% modulus of a particular formulation from 310 psi to 780 psi. The stiffness of catheters can thus be increased about 150 percent.

EXAMPLE 48

Yet another water-based aliphatic polyisoprene dispersion, AMPUD-12a (from Ortec, Inc.) is blended with 5 and 10%

(of the amount of polyisoprene) of polyurethane. The resulting 500% modulus for the different blends is shown in Table 61 below.

TABLE 61

| | Percent of Polyurethane Added | | |
|---|---|---|---|
| | 0 | 5 | 10 |
| 500% Modulus, psi | 316 | 577 | 958 |

Table 61 shows that adding 5% of polyurethane can increase the 500% modulus of a particular formulation from 316 psi to 577 psi. The stiffness of catheters formed using this formulation can be thus increased about 83 percent. Adding 10% of polyurethane can increase the 500% modulus of a particular formulation from 316 psi to 958 psi. The stiffness of catheters can thus be increased about 200 percent.

EXAMPLE 49

Another water-based aliphatic polyisoprene dispersion, Hauthane L-2245 from Hauthaway Corp. of Lynn, Mass.), is blended with 5 and 10% (of the amount of polyisoprene) of polyurethane. The resulting 500% modulus for the different blends is shown in Table 62 below.

TABLE 62

| | Percent of Polyurethane Added | | |
|---|---|---|---|
| | 0 | 5 | 10 |
| 500% Modulus, psi | 305 | 581 | 800 |

Table 62 shows that adding 5% of polyurethane can increase the 500% modulus of a particular formulation from 305 psi to 581 psi. The stiffness of catheters formed using this formulation can be thus increased about 90 percent. Adding 10% of polyurethane can increase the 500% modulus of a particular formulation from 305 psi to 800 psi. The stiffness of catheters can thus be increased about 160 percent.

EXAMPLE 50

In this example, synthetic polyisoprene is compounded with 0.1 phr potassium hydroxide, 2 phr sulfur, 1 phr of a sulfur donor, 0.5 phr zinc mercaptobenzothiazole, 0.1 phr sodium dibutyl dithiocarbamate, 1.5 phr zinc oxide, and 1.0 phr hindered phenol. The compounded synthetic polyisoprene is then blended with 20, 40, 60 and 80 percent of anionic, aliphatic, aqueous polyurethane, and medical articles are formed from the blends. The 300% modulus of the articles is measured at 21° C. The articles are then immersed in a 37.8° C. (approximately body temperature) water tank for 1 hour, and the 300% modulus is measured again. The resulting 300% modulus for the different blends, at different temperatures, is shown in Table 63 below.

TABLE 63

| | Percent of Polyurethane Added | | | | |
|---|---|---|---|---|---|
| | 0 | 20 | 40 | 60 | 80 |
| 300% Modulus, psi at 21° C. | 400 | 654 | 954 | 1272 | 1450 |
| 300% Modulus, psi at 37.8° C. | 380 | 580 | 750 | 860 | 950 |

Table 63 shows that adding 20% of polyurethane can increase the 300% modulus of a particular formulation, at 21° C., from 400 psi to 654 psi (an increase in stiffness of about 64 percent). Adding 80% of polyurethane can increase the 300% modulus of the same formulation, at 21° C., from 400 psi to 1450 psi (an increase in stiffness of about 260 percent). Table 63 also shows that, for each of the blends, increasing the temperature of the medical article from room temperature to body temperature can lower the 300% modulus significantly.

EXAMPLE 51

In this example, synthetic polyisoprene is compounded with 0.2 phr potassium hydroxide, 2 phr sulfur, 1 phr of a sulfur donor, 0.1 phr sodium dibutyl dithiocarbamate, 0.5 phr zinc oxide, and 0.5 phr hindered phenol. The compounded synthetic polyisoprene is then blended with 2.5, 7.5, and 10 percent of anionic, aliphatic, aqueous polyurethane, and medical articles are formed from the blends. The 300% modulus of the articles is measured at 21° C. The articles are then immersed in a 37.8° C. (approximately body temperature) water tank for 1 hour, and the 300% modulus is measured again. The resulting 300% modulus for the different blends, at different temperatures, is shown in Table 64 below.

TABLE 64

| | Percent of Polyurethane Added | | | |
|---|---|---|---|---|
| | 0 | 2.5 | 7.5 | 10 |
| 300% Modulus, psi at 21° C. | 142 | 222 | 348 | 368 |
| 300% Modulus, psi at 37.8° C. | 170 | 214 | 323 | 327 |

Table 64 shows that adding 7.5% of polyurethane can increase the 300% modulus of a particular formulation, at 21° C., from 142 psi to 348 psi (an increase in stiffness of about 145 percent). Adding 10% of polyurethane can increase the 300% modulus of the same formulation, at 21° C., from 142 psi to 368 psi (an increase in stiffness of about 160 percent). Table 64 also shows that, for each of the blends, increasing the temperature of the medical article from room temperature to body temperature can lower the 300% modulus.

The various embodiments of SPIR and SPIR/polyurethane blend catheters 1, 14 described above thus provide a number of advantages over known catheters. Of course, it is to be understood that not necessarily all such objectives or advantages may be achieved in accordance with any particular embodiment of the SPIR catheters described herein. Thus, for example, those skilled in the art will recognize that the SPIR catheter may be developed in a manner that achieves or optimizes one advantage or group of advantages as taught herein without necessarily achieving other objectives or advantages as may be taught or suggested herein.

Although illustrated within the context of an intermittent catheter 1 and Foley catheter 14, embodiments of the present invention may also be used with other medical article for which varying rigidity and flexibility at different temperatures is desirable. It will be understood by those of skill in the art that numerous and various modifications can be made without departing from the spirit of the present invention.

It is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims which follow.

What is claimed is:

1. A method of manufacturing an intermittent urinary drainage catheter, the method comprising:
   mixing synthetic polyisoprene with compounding ingredients to produce compounded synthetic polyisoprene;
   maturation of the compounded synthetic polyisoprene;
   mixing the compounded synthetic polyisoprene with polyurethane to form a blend; and
   dipping a mold in the blend to form the catheter, the rigidity of the catheter varying with temperature, wherein at least a portion of the catheter has a glass transition temperature of between about 25° C. and about 36° C.

2. The method of claim 1 further comprising:
   dipping the mold in a coagulant;
   drying the mold; and
   leaching the dipped mold in water.

3. The method of claim 1 further comprising:
   drying the mold in an oven;
   removing the mold;
   allowing the mold to cool; and
   stripping the catheter from the mold.

4. The method of claim 1 further comprising compounding an accelerator system.

5. The method of claim 4, wherein the accelerator system comprises a carbamate, a thiazole and a guanidine.

6. The method of claim 4, wherein the accelerator system is compounded before the compounded synthetic polyisoprene is mixed with the polyurethane.

7. The method of claim 4, wherein the accelerator system comprises a carbamate and a thiazole.

8. The method of claim 4, wherein the accelerator system comprises a carbamate.

9. The method of claim 4, wherein the accelerator system comprises a guanidine.

10. The method of claim 4, wherein the accelerator system comprises a thiazole and a guanidine.

11. The method of claim 4, wherein the accelerator system comprises a carbamate and a guanidine.

12. The method of claim 1 further comprising compounding a vulcanizing system.

13. The method of claim 12, wherein the vulcanizing system is compounded before the compounded synthetic polyisoprene is mixed with the polyurethane.

14. The method of claim 13, wherein the vulcanizing system comprises a sulfur and a dipentamethylenethiuram hexasulfide (DPTH).

15. The method of claim 13, wherein the vulcanizing system comprises a sulfur.

16. The method of claim 13, wherein the vulcanizing system comprises a dipentamethylenethiuram hexasulfide.

* * * * *